United States Patent [19]

Inoue et al.

[11] Patent Number: 5,116,855
[45] Date of Patent: May 26, 1992

[54] RHODANINE DERIVATIVES AND PHARMACEUTICAL COMPOSITIONS

[75] Inventors: Hitoshi Inoue; Hiroki Kato; Noriyoshi Sueda; Yoshiyuki Tahara; Nobuhiro Kinoshita, all of Saitama, Japan

[73] Assignee: Nisshin Flour Milling Co., Ltd., Tokyo, Japan

[21] Appl. No.: 521,902

[22] Filed: May 11, 1990

[30] Foreign Application Priority Data

May 19, 1989 [JP] Japan .................. 1-124252
May 1, 1990 [JP] Japan .................. 2-111761

[51] Int. Cl.⁵ .................. C07D 277/34; A01K 31/425
[52] U.S. Cl. .................. 514/369; 598/183
[58] Field of Search .................. 548/183; 514/369

[56] References Cited

U.S. PATENT DOCUMENTS 4,897,406  1/1990  Inoue .................. 514/369

FOREIGN PATENT DOCUMENTS 0047109  8/1981  European Pat. Off. .
0143461  11/1984  European Pat. Off. .
0316790  11/1988  European Pat. Off. .
57-28074  2/1982  Japan .
60-136575  7/1985  Japan .
60-156387  8/1985  Japan .
64-52765  2/1989  Japan .

OTHER PUBLICATIONS

Chemical Abstracts, vol. III, No. 18, Oct. 30, 1989, 163902V.
Chemical Abstracts, vol. III, No. 17, Oct. 23, 1989, 153788y.

Primary Examiner—Robert Gerstl
Attorney, Agent, or Firm—Abelman Frayne and Schwab

[57] ABSTRACT

Disclosed is a rhodanine derivative of formula (I).

A rhodanine derivative of formula (I)

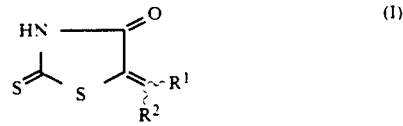

wherein
$R^1$ is hydrogen, $C_1-C_8$ alkyl, carboxyl($C_1-C_4$)alkyl or ($C_1-C_4$)alkoxycarbonyl($C_1-C_4$)alkyl;
$R^2$ is $-CH_2-CH_2-R^3$, $-(CH=CH)_m-R^3$ (m is 0 or 1),

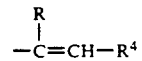

(R is $C_1-C_3$ alkyl) or $-(CH_2)_n-CONHR^4$ (n is 0 or 1–4);
$R^3$ is a thienyl or furyl group which may be substituted by $C_1-C_3$ alkyl or halogen; a pyrrolyl group which may be substituted by carboxy($C_1-C_3$)alkyl on the nitrogen atom; or a phenyl group which may be substituted by one or more substituents selected from the group consisting of $C_1-C_3$ alkyl, $C_1-C_3$ alkoxy, hydroxyl, halogen, trifluoromethyl, carboxyl, ($C_1-C_3$)alkoxycarbonyl, cyano, carboxy($C_1-C_3$)alkoxy, ($C_1-C_6$)alkoxycarbonyl($C_1-C_3$)alkoxy, benzyloxycarbonyl($C_1-C_3$)alkoxy, piperidinylcarbonyl($C_1-C_3$)alkoxy, 2H-tetrazolyl, 2H-tetrazolyl-($C_1-C_4$)alkoxy, carboxy($C_2-C_4$)alkenyl, ($C_1-C_3$)alkoxycarbonyl($C_2-C_4$)alkenyl, carboxy($C_1-C_3$)alkyl and ($C_1-C_3$)alkoxycarbonyl($C_1-C_3$)alkyl; and
$R^4$ is a phenyl group which may be substituted by one or more of the same substituents as defined above, or a pharmaceutically acceptable salt thereof.

The derivatives are of an inhibitory activity against aldose reductase and useful for the prevention or treatment of complications of diabetes.

6 Claims, No Drawings

RHODANINE DERIVATIVES AND PHARMACEUTICAL COMPOSITIONS

FIELD OF THE INVENTION

This invention relates to new rhodanine derivatives, processes for preparing the same and pharmaceutical compositions having an inhibitory activity against aldose reductase which comprise said derivatives as an active ingredient.

BACKGROUND OF THE INVENTION

An aldose reductase is an enzyme which catalyzes the conversion of aldose in vivo, e.g. glucose or galactose into its corresponding polyol, e.g. sorbitol or galactitol, respectively. It is known that the sorbitol and galactitol produced by the action of this enzyme are accumulated in the lenses, the peripheral nerves, the kidney, etc., of diabetics and galactosemiacs, thus causing complications of diabetes, e.g. retinopathy, diabetic cataract, neuropathy and nephropathy. Thus the inhibition of the enzyme aldose reductase permits the prevention or treatment of the above-described complications.

Japanese Patent Application Kokai Nos. 57-28074, 60-156387 (EP-A 0 047 109) and 60-136575 (EP-A 0 143 461) disclose that rhodanine derivatives possess an inhibitory activity against aldose reductase. However the compounds disclosed therein are structurally different from those of the present invention in respect of the nitrogen atom on the rhodanine ring being substituted.

Japanese Patent Application Kokai No. 64-52765 discloses that the compounds wherein the nitrogen atom on the rhodanine ring is not substituted possess an inhibitory activity against aldose reductase. However those compounds are also structurally different from the compounds of the present invention with respect of the substituents attached to the 5-position through a double bond.

DISCLOSURE OF THE INVENTION

The rhodanine derivatives of the present invention are represented by formula (I)

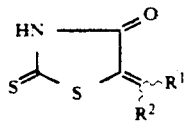

wherein $R^1$ is hydrogen, $C_1-C_8$ alkyl, carboxy($C_1-C_4$)alkyl or ($C_1-C_4$)alkoxycarbonyl($C_1-C_4$)alkyl;
$R^2$ is $-CH_2-CH_2-R^3$, $-(CH=CH)_m-R^3$ (m is 0 or 1),

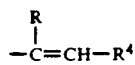

(R is $C_1-C_3$ alkyl) or $-(CH_2)_n-CONHR^4$ (n is 0 or 1–4);
$R^3$ is a thienyl or furyl group which may be substituted by $C_1-C_3$ alkyl or halogen; a pyrrolyl group which may be substituted by carboxy($C_1-C_3$)alkyl on the nitrogen atom; or a phenyl group which may be substituted by one or more substituents selected from the group consisting of $C_1-C_3$ alkyl, $C_1-C_3$ alkoxy, hydroxyl, halogen, trifluoromethyl, carboxyl, ($C_1-C_3$)alkoxycarbonyl, cyano, carboxy($C_1-C_3$)alkoxy, ($C_1-C_6$)alkoxycarbonyl($C_1-C_3$)alkoxy, benzyloxycarbonyl($C_1-C_3$)alkoxy, piperidinylcarbonyl($C_1-C_3$)alkoxy, 2H-tetrazolyl, 2H-tetrazolyl-($C_1-C_4$)alkoxy, carboxy($C_2-C_4$)alkenyl, ($C_1-C_3$)alkoxycarbonyl($C_2-C_4$)alkenyl, carboxy($C_1-C_3$)alkyl and ($C_1-C_3$)alkoxycarbonyl($C_1-C_3$)alkyl; and
$R^4$ is a phenyl group which may be substituted by one or more of the same substituents as defined above.

The compounds of the present invention, in the case of having an acid radical therein, can form their salts with pharmaceutically acceptable inorganic or organic bases and the salts are also included in the scope of the present invention.

The compounds of the present invention contain an asymmetric carbon atom or a double bond in the substituent at the 5-position of the rhodanine ring and there are therefore an optical isomer based on the asymmetric carbon atom or cis, trans isomers based on the double bond. Thus these isomers and the mixtures thereof are also included in the scope of the present invention.

The groups included in the definition of formula (I) are further illustrated below.

$C_1-C_8$ alkyl in the definition of $R^1$ includes straight or branched chain alkyl, e.g. methyl, ethyl, n-propyl, isopropyl, n-butyl, sec-butyl, isobutyl, tert-butyl, n-amyl, n-hexyl, n-heptyl and n-octyl.

Carboxy($C_1-C_4$)alkyl in the definition of $R^1$ includes e.g. $-CH_2COOH$, $-(CH_2)_2COOH$, $-(CH_2)_3COOH$ or $-(CH_2)_4COOH$, $-(C_1-C_4)$alkoxycarbonyl($C_1-C_4$)alkyl includes e.g. $-CH_2COOCH_3$, $-CH_2COOC_2H_5$, $-CH_2COOC_3H_7$, $-CH_2COOC_4H_9$, $-(CH_2)_2COOCH_3$, $-(CH_2)_2COOC_2H_5$, $-(CH_2)_2COOC_3H_7$, $-(CH_2)_2COOC_4H_9$, etc.

Of the substituents on the phenyl group in the definition of $R^3$, ($C_1-C_3$)alkoxycarbonyl includes e.g. $-COOCH_3$, $-COOC_2H_5$, $-COOC_3H_7$, etc.; carboxy($C_1-C_3$)alkoxy includes e.g. $-OCH_2COOH$, $-O(CH_2)_2COOH$, $-O(CH_2)_3COOH$, etc.; and ($C_1-C_6$)alkoxycarbonyl($C_1-C_3$)alkoxy includes e.g. $-OCH_2COOCH_3$, $-OCH_2COOC_2H_5$, $-OCH_2COO(CH_2)_3CH_3$, etc. Representative example of benzyloxycarbonyl($C_1-C_3$)alkoxy is

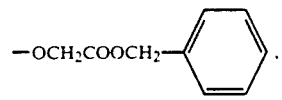

etc.; that of piperidinylcarbonyl($C_1-C_3$)alkoxy is

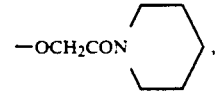

etc.; and that of 2H-tetrazolyl($C_1-C_4$)alkoxy is

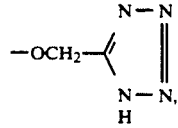

etc. Representative example of carboxy($C_2-C_4$)alkenyl is $-CH=CH-COOH$, etc.; and that of ($C_1-C_3$) alkoxycarbonyl($C_2-C_4$)alkenyl is $-CH=CH-COOCH_3$, $-CH=CH-COOC_2H_5$, etc. Representative example of carboxy($C_1-C_3$)alkyl includes $-CH_2COOH$, —(CH$_2$)$_2$COOH, —(CH$_2$)$_3$COOH, etc. and that of (C$_1$-C$_3$)alkoxycarbonyl(C$_1$-C$_3$)alkyl includes —(CH$_2$)$_2$COOCH$_3$, —(CH$_2$)$_2$COOC$_2$H$_5$, etc.

Representative examples of substituted thienyl, furyl and pyrrolyl groups in the definition of R$^3$ include 3-methyl-2-thienyl, 4-methyl-2-thienyl, 5-methyl-2-thienyl, 4-chloro-2-thienyl, 5-chloro-2-thienyl, 3-methyl-2-furyl, 4-methyl-2-furyl, 5-methyl-2-furyl, 4-chloro-2-furyl, 2-(N-carboxymethyl)-pyrrolyl, 2-(N-carboxyethyl)-pyrrolyl, etc.

Representative examples of substituted phenyl groups in the definition of R$^3$ and R$^4$ include 2-, 3- or 4-tolyl, 3- or 4-ethylphenyl, 2-, 3- or 4-hydroxyphenyl, 2-, 3- or 4-methoxyphenyl, 4-hydroxy-3-methoxyphenyl, 3-hydroxy-4-methoxyphenyl, 3,4-dimethoxyphenyl, 4-isopropoxy-3-methoxyphenyl, 3,4,5-trimethoxyphenyl, 3-tert-butyl-4-hydroxyphenyl, 4-hydroxy-3,5-diisopropylphenyl, 3,5-di-tert-butyl-4-hydroxyphenyl, 2-, 3- or 4-fluorophenyl, 2-, 3- or 4-chlorophenyl, 3,4-dichlorophenyl, 2-, 3- or 4-trifluoromethylphenyl, 2-, 3- or 4-carboxyphenyl, 3- or 4-cyanophenyl, 4-aminophenyl, 4-(N,N-dimethyl)aminophenyl, 2-, 3-or 4-methoxycarbonylphenyl, 4-carboxymethoxyphenyl, 4-methoxy-4-carboxymethoxyphenyl, 4-methoxycarbonylmethoxyphenyl, 4-ethoxycarbonylmethoxyphenyl, 2- or 3-carboxymethoxyphenyl, 2- or 3-methoxycarbonylmethoxyphenyl, 2-, 3- or 4-ethoxycarbonylmethoxyphenyl, 4-carboxyvinylphenyl, 4-ethoxycarbonylvinylphenyl, 4-carboxyethylphenyl, 4-ethoxycarbonylethylphenyl, 4-(2H-tetrazolyl)-methoxyphenyl, 4-(2H-tetrazolyl)-phenyl, 4-(2H-tetrazolyl)-butyleneoxyphenyl, 4-ethoxycarbonylmethoxy-3-methoxyphenyl, 4-methoxycarbonylmethoxy-3-methoxyphenyl, 3-ethoxy-4-methoxycarbonylmethoxyphenyl, 3-methoxycarbonylmethoxy-2-methoxyphenyl, 3-methoxycarbonylmethoxy-4-methoxyphenyl, 2-methoxycarbonylmethoxy-4-methoxyphenyl, 3,4-dimethoxycarbonylmethoxyphenyl, 4-carboxymethoxy-3-ethoxyphenyl, 3-carboxymethoxy-4-methoxyphenyl, 3-carboxymethoxy-4-methoxyphenyl, 2-carboxymethoxy-4-methoxyphenyl, 3,4-dicarboxymethoxyphenyl, 5-isopropyl-2-methoxycarbonylmethoxyphenyl, 5-chloro-2-methoxycarbonylmethoxyphenyl, 2-benzyloxycarbonylmethoxy-5-chlorophenyl, 5-chloro-2-piperidynylcarbonylmethoxyphenyl, 5-bromo-2-methoxycarbonylmethoxyphenyl, 3,5-dichloro-2-methoxycarbonylmethoxyphenyl, 2-carboxymethoxy-5-isopropylphenyl, 2-carboxymethoxy-5-chlorophenyl, 5-bromo-2-methoxycarbonylmethoxyphenyl, 5-carboxymethoxy-3,5-dichlorophenyl, 3,5-dibromo-2-methoxycarbonylmethoxyphenyl, 2-methoxycarbonylmethoxy-5-trifluoromethylphenyl, 3,5-dimethoxy-4-methoxycarbonylmethoxyphenyl, 3,5-dimethyl-4-methoxycarbonylmethoxyphenyl, 4-ethoxycarbonylmethoxy-3,5-diisopropylphenyl, 3,5-dibromo-2 carboxymethoxyphenyl, 2-carboxymethoxy-5-trifluoromethylphenyl, 4-carboxymethoxy-3,5-dimethoxyphenyl, 4-carboxymethoxy-3,5-dimethylphenyl and 4-carboxymethoxy-3,5-diisopropylphenyl.

The compounds of formula (I) can be prepared by reacting rhodanine of formula (II)

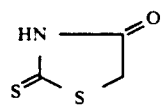

with an aldehyde or ketone of formula (III)

wherein R$^1$ and R$^2$ have the same meanings as defined above.

In this reaction, the aldehyde or ketone of formula (III) may be employed in the range of 0.5 to 10 moles per mole of rhodanine of formula (II), but both may be usually employed in equimolar amounts. The aldehyde or ketone is preferably used in a slightly excess amount relative to rhodanine, e.g. 1.1 to 1.5 moles per mole of rhodanine of formula (II).

The reaction may be carried out without any solvents or preferably in the presence of an organic solvent. The organic solvents used include hydrocarbons such as n-hexane, ligroin, benzene, toluene, etc.; lower alcohols such as methanol, ethanol, isopropanol, etc.; ether solvents such as ether, tetrahydrofuran, dioxane, etc.; esters such as ethyl acetate, butyl acetate, etc.; chlorinated hydrocarbons such as ethylene dichloride, chloroform, trichloroethylene, carbon tetrachloride, etc.; aprotic polar solvents such as dimethyl sulfoxide, dimethylformamide, diethylformamide, dimethylacetamide, etc.; and protic polar solvents such as formic acid, acetic acid, etc.; and such solvents may be employed alone or in combination with two or more thereof.

The reaction may be carried out at any temperature and preferably under heating. Generally, the reaction may be carried out at a temperature of 50 to 150° C, depending upon the solvents to be employed. Further, the reaction is preferably conducted at a temperature in the neighborhood of the boiling point of the solvent employed, which is easily controllable for the reaction temperature.

Preferably, a catalyst may be added for promoting the reaction. The catalysts used include ammonia; secondary amines such as piperidine, diethylamine, etc.; salts of organic acids such as ammonium acetate, sodium acetate, etc. Such catalysts may be employed alone or in combination with two or more thereof. These catalysts may be used in the range of 0.2 to 5 moles per mole of rhodanine of formula (II), with the range of 1.0 to 1.5 moles being preferred.

The reaction will be completed in 1 to 12 hours, depending upon the reactivity of reactants employed and such conditions as reaction temperature, etc.

The reaction product may be separated from the reaction mixture obtained as above according to any conventional means in the art. For instance, the reaction product can be isolated by such means as concentration of the reaction mixture followed by separation by recrystallization or chromatography, etc.

If necessary, the compounds of formula (I) can be converted into the pharmaceutically acceptable salts in a conventional manner by using pharmaceutically acceptable inorganic or organic bases. Examples of the bases include hydroxides or carbonates of alkali metals such as sodium, potassium, etc. or alkaline earth metals such as magnesium, calcium, etc.; aluminum hydroxide; ammonia; ammonium carbonate; primary amines such as methylamine, ethylamine, etc.; secondary amines such as diethylamine, morpholine, etc.; and tertiary amines such as triethylamine, pyridine, etc.

The rhodanine derivatives of formula (I) and the pharmaceutically acceptable salts thereof have an inhibitory activity against aldose reductase which catalyzes the conversion of an aldose into the corresponding polyol, thus inhibiting an abnormal increase in sorbitol content in cells of diabetic patients. Thus the compounds of formula (I) and their salts of the present invention are useful for the prevention and treatment of diabetic complications, e.g. retinopathy, diabetic cataract, neuropathy and nephropathy.

The compounds of the present invention exhibited a significant inhibitory activity against aldose reductase at $10^{-5}$ to $10^{-6}$ molar concentrations, for example according to experiments in a laboratory conducted in accordance with the modification (Biochemical Pharmacology, 25, 2505 (1976)) of the method described in J. Biol. Chem., 240, 877 (1965) using an aldose reductase obtained from rat lenses.

Thus the present invention provides pharmaceutical compositions which comprise as an active ingredient the rhodanine derivatives of formula (I) or the pharmaceutically acceptable salts thereof.

The pharmaceutical compositions can be formulated into solid, semi-solid or liquid preparations in a usual manner using conventional pharmaceutically acceptable carriers. The pharmaceutical preparations may be administered orally or parenterally. Such preparations may include tablets, capsules, suppositories, troches, syrups, creams, ointments, plasters, cataplasms, granules, powders, injections, suspensions, inhalations, aerosols and the like. They may be formed into double layer tablets or multilayer tablets with other drugs. Further, tablets may be formed, if necessary, into tablets having usual coated films, e.g. sugar-coated tablets, enteric-coated tablets, film-coated tablets. Examples of the carriers include e.g. excipients, binders, diluents and lubricants, typical examples of which are lactose, starch, sugar, microcrystalline cellulose, magnesium stearate, silicon dioxide, talc, physiological salt solution and sterilized water.

The pharmaceutical preparations may contain 0.1 to 100% by weight of the active ingredient and suitably 1 to 50% by weight for oral administration and 0.1 to 10% by weight for injection.

The active compounds are effective over a wide dosage range. For example, dosages per day will normally fall within the range of 0.001 to 1000 mg/kg-body weight, but the amount of the compound actually administered will be determined by a physician in the light of the relevant circumstances including the condition to be treated, the route of administration, age, sex, severity of the patient's symptoms, etc.

The invention is further illustrated by the following non-limitative example.

EXAMPLE 1

Ethyl 4-[3-(4-oxo-2-thioxo-5-thiazolidinylidene)-1-butenyl]-phenoxyacetate

A mixture of 1.33 g (0.01 mol) of rhodanine, 2.48 g (0.01 mol) of ethyl 4-(3-oxo-1-butenyl)phenoxycetate, 0.77 g (0.01 mol) of ammonium acetate and 20 ml of toluene was heated under reflux for 3 hours. After cooling, 100 ml of water were added to the reaction mixture which was extracted with ethyl acetate (3×100 ml). The ethyl acetate layer was washed twice with water and once with a saturated saline solution, dried and concentrated under reduced pressure to give orange crystals. The crystals were purified by silica gel column chromatography (eluent, chloroform: ethyl acetate) to obtained 0.28 g (7.7% yield) of Isomer A of ethyl 4-[3-(4-oxo-2-thioxo-5-thiazolidinylidene)-1-butenyl]phenoxyacetate from the first eluate and 0.48 g (13.2% yield) of Isomer B from the subsequent eluate.

Isomer A

Yellow crystals, m.p. 209°-213° C. (dec.)
Mass spectrum (m/e): 363 (M$^-$)
NMR(DMSO-d$_6$) δ: 1.22(t, 3H), 2.50(s, 3H), 4.17(q, 2H), 4.80(s, 2H), 6.65(d, 1H, J=16Hz), 6.95 (d, 2H), 7.32(d, 1H, J=16Hz), 7.68(d, 2H), 13.40(br, s, 1H)
IR(KBr) cm$^{-1}$: 1740, 1680, 1603, 970, 959

Isomer B

Yellow crystals, m.p. 220°-223° C. (dec.)
Mass spectrum (m/e): 363 (M$^+$)
NMR(DMSO-d$_6$) δ: 1.22(t, 3H), 2.16(s, 3H), 4.20(q, 2H), 4.80(s, 2H), 7.00(d, 2H), 7.28(d, 1H, J=16Hz), 7.54(d, 2H), 8.45(d, 1H, J=16Hz), 13.45(br, s, 1H)
IR(KBr) cm$^{-1}$: 1772, 1689, 1604, 981, 926

In accordance with similar procedure as mentioned in Example 1, the compounds shown in the following Examples to 20 were obtained from the corresponding aldehydes or ketones.

EXAMPLE 2

Ethyl 6-(3,4-dimethoxyphenyl)-4-(4-oxo-2-thioxo-5-thiazolidinylidene)-5-hexenoate Yield 7%
NMR(CDCl$_3$) δ: 1.30(t, 3H), 2.50-2.65(m, 2H), 2.75-290(m, 2H), 3.92(s, 3H), 3.95(s, 3H), 4.18(q, 2H), 6.80-7.20(m, 4H), 8.47(d, 1H, J=16Hz), 9.75(br, s, 1H)
IR(KBr) cm$^{-1}$: 1730, 1671, 1540, 979

EXAMPLE 3

4-[3-(4-Oxo-2-thioxo-5-thiazolidinylidene)-1-hexenyl]-benzoic acid

Isomer A

Yield 6%
Yellow crystals, m.p. 278°-280° C. (dec.)
Mass spectrum (m/e): 333 (M$^-$)
NMR(DMSO-d$_6$) δ: 1.00(t, 3H), 1.45-1.70(m, 2H), 7.40(d, 1H, J=16Hz), 7.70(d, 2H, J=8Hz), 7.95(d, 2H, J=8Hz), 8.58(d, 1H, J=16Hz), 3.00(br, s, 1H), 3.60(br, s, 1H)
IR(KBr) cm$^{-1}$: 1695, 1680, 1605, 980

Isomer B

Yield 6%
Yellow crystals, m.p. 257°-261° C. (dec.)
Mass spectrum (m/e): 333 (M$^+$)
IR(KBr) cm$^{-1}$: 1690, 1605, 1540, 945

EXAMPLE 4

5-[α-Hexyl-4-(1H tetrazol-5-yl)methoxycinnamilidene-4-oxo-2-thioxothiazolidine

Yield 9%
Brown crystals, m.p. above 300° C.
NMR(DMSO-d$_6$) δ: 0.80-1.00(m, 3H), 1.20-1.60(m, 8H), 2.35-2.50(m, 2H), 5.24(s, 2H), 7.05-7.20(m, 3H), 7.50(d, 2H), 8.50(d, 1H, J=16Hz)
IR(KBr) cm$^{-1}$: 3400, 1675, 1600, 1573, 970

EXAMPLE 5

Ethyl 6-(2-fluorophenyl)-4-(4-oxo-2-thioxo-5-thiazolidinylidene)-5-hexenoate

Isomer A

Yield 13.5%, m.p. 159°-161° C. (dec.)
NMR(CDCl$_3$) δ: 1.29(t, 3H), 2.60(q, 2H), 2.86(q, 2H), 4.19(q, 2H), 7.00-7.40(m, 3H), 7.32(d, 1H, J=16.6Hz), 7.72(t×d, 1H), 8.59(d, 1H, J=16.6Hz), 8.33(bs, 1H)
IR(KBr) cm$^{-1}$: 3158, 1728, 1680, 1608, 1547, 1485, 1074, 1027, 963, 761

Isomer B

Yield 4.3%, m.p. 163°-164.5° C. (dec.)
NMR(CDCl$_3$) δ: 1.27(t, 3H), 2.58(t, 2H), 3.43(t, 2H), 4.15(q, 2H), 6.75(d, 1H, J=15.6Hz), 7.05-7.45(m, 4H), 7.56(t×d, 1H), 9.34(bs, 1H)
IR(KBr) cm$^{-1}$: 3402, 1715, 1694, 1602, 1544, 1067, 966, 764

EXAMPLE 6

Ethyl 6-(4-trifluoromethylphenyl)-4-(4-oxo-2-thioxo-5-thiazolidinylidene)-5-hexenoate

Isomer A

Yield 10%, m.p. 172°-174° C. (dec.)
NMR(CDCl$_3$) δ: 1.29(t, 3H), 2.60(t, 2H), 2.86(t, 2H), 4.19(q, 2H), 7.12(d, 1H, J=16.6Hz), 7.62(d, 2H), 7.69(d, 2H), 8.64(d, 1H, J=16.6Hz), 9.50(bs, 1H)
IR(KBr) cm$^{-1}$: 3418, 1724, 1679, 1617, 1550, 1330, 1199, 1122, 1069, 990, 827

Isomer B

Yield 2%, m.p. 171°-174° C. (dec.)
NMR(CDCl$_3$) δ: 1.27(t, 3H), 2.58(t, 2H), 3.43(t, 2H), 4.15(q, 2H), 6.71(d, 1H, J=15.6Hz), 7.27(d, 1H, J=15.6Hz), 7.57-7.64(m, 4H), 9.23(bs, 1H)
IR(KBr) cm$^{-1}$: 3414, 1734, 1711, 1618, 1554, 1439, 1329, 1201, 1070

EXAMPLE 7

Ethyl 6-(4-cyanophenyl)-4-(4-oxo-2-thioxo-5-thiazolidinylidene)-5-hexenoate

Yield 17.8%, m.p. 196°-200° C. (dec.)
NMR(CDCl$_3$) δ: 1.28(t, 3H), 2.58(t, 2H), 2.85(t, 2H), 4.18(q, 2H), 7.08(d, 1H, J=16.6Hz), 7.66(s, 4H), 8.65(d, 1H, J=16.6Hz), 9.46(bs, 1H)
IR(KBr) cm$^{-1}$: 3416, 2222, 1720, 1678, 1544, 1211, 1074, 824

EXAMPLE 8

Ethyl 6-(3-hydroxyphenyl)-4-(4-oxo-2-thioxo-5-thiazolidinylidene)-5-hexenoate

Isomer A

Yield 6%, m.p. 200°-205° C. (dec.)
NMR(CDCl$_3$-DMSO-d$_6$) δ: 1.26(t, 3H), 2.55(t, 2H), 3.38(t, 2H), 4.13(q, 2H), 6.60(d, 1H, J=16Hz), 6.80-7.30(m, 5H), 8.99(s, 1H), 12.80(bs, 1H)
IR(KBr) cm$^{-1}$: 3588, 3514, 1712, 1702, 1611, 1580, 1552, 1494, 1456, 1264, 1068, 959

Isomer B

Yield 11.8%, m.p. 197°-199° C. (dec.)
NMR(CDCl$_3$+DMSO-d$_6$) δ: 1.28(t, 3H), 2.50-2.90(m, 4H), 4.17(q, 2H), 6.75-7.30(m, 5H), 8.55(q, 1H, J=16Hz), 8.92(s, 1H), 12.80(bs, 1H)

EXAMPLE 9

Methyl 4-[3-(4-oxo-2-thioxo-5-thiazolidinylidene-1-nonenyl]-benzoate

Isomer A

Yield 5%, m.p. 175°-176° C.
Mass spectrum (m/e); 389 (M$^-$)
NMR(CDCl$_3$) δ: 0.85-1.00(m, 3H), 1.20-1.70(m, 8H), 3.10(t, 2H), 3.94(s, 3H), 6.74(d, 1H, J=15.6Hz), 7.18(d, 1H, J=15.6Hz), 7.58(d, 2H), 8.07(d, 2H), 9.45(bs, 1H)
IR(KBr) cm$^{-1}$: 3412, 3148, 1721, 1684, 1610, 1545, 1283, 1222, 1111, 1075, 1017, 950, 768

Isomer B

Yield 17%, m.p. 148°-150° C.
Mass spectrum (m/e); 389 (M$^+$)
NMR(CDCl$_3$) δ: 0.85-1.00(m, 3H), 1.25-1.70(m, 8H), 2.50(t, 2H), 3.93(s, 3H), 7.08(d, 1H, J=16.6Hz), 7.65(d, 2H), 8.05(d, 2H), 8.68(d, 1H, J=16.6Hz), 9.80(bs, 1H)
IR(KBr) cm$^{-1}$: 3166, 1706, 1609, 1552, 1441, 1281, 1195, 1111, 1065, 970, 879, 769

EXAMPLE 10

Ethyl 2-[3-(4-oxo-2-thioxo-5-thiazolidinylidene)hexyl]-phenoxyacetate

Isomer A

Yield 50%, m.p. 109°-110.3° C. (CH$_2$Cl$_2$-IPE)
NMR(CDCl$_3$) δ: 1.00(t, 3H), 1.30(t, 3H), 1.55(m, 2H), 2.52(m, 2H), 2.80-2.95(m, 4H), 4.27(q, 2H), 4.69(s, 2H), 6.72(d, 1H), 6.92(t, 1H), 7.07-7.25(2H), 9.02(bs, 1H)
IR(KBr) cm$^{-1}$: 3380, 3120, 1710, 1605, 1445, 1195, 760

Isomer B

Yield 25%, m.p. 121.6°-122.5° C. (CHCl$_3$-IPE)
NMR(CDCl$_3$) δ: 0.98(t, 3H), 1.30(t, 3H), 1.60(m, 2H), 2.19(m, 2H), 2.90(m, 2H), 3.11(m, 2H), 4.26(q, 2H), 4.63(s, 2H), 6.72(d, 1H), 6.94(t, 1H), 7.10-7.30(2H), 9.22(bs, 1H)
IR(KBr) cm$^{-1}$: 3450, 3060, 1758, 1695, 1600, 1460, 1215, 755, 675

EXAMPLE 11

Ethyl 4-[3-(4-oxo-2-thioxo-5-thiazolidinylidene)-1-nonenyl]-cinnamate

Isomer A

Yield 2.4%, m.p. 187.5°-189.0° C. (CH$_2$Cl$_2$-IPE)
NMR(CDCl$_3$) δ: 0.90(t, 3H), 1.34(t, 3H), 1.25-1.60(8H), 3.10(t, 2H), 4.28(q, 2H), 6.49(d, 1H), 6.70(d, 1H), 7.14(d, 1H), 7.56(s, 4H), 7.67(d, 1H), 9.03(bs, 1H)
IR(KBr) cm$^{-1}$: 3430, 3130, 3020, 1710, 1680, 1635, 1540, 1305, 1210, 680

Isomer B

Yield 6.5%, m.p. 199.5°–200.2° C. (CH$_2$Cl$_2$-IPE)
NMR(CDCl$_3$) δ: 0.91(t, 3H), 1.36(t, 3H), 1.25–1.67(8H), 2.50(t, 2H), 4.28(q, 2H), 6.48(d, 1H), 7.08(d, 1H), 7.58(q, 4H), 7.69(d, 1H), 8.63(d, 1H), 9.30(bs, 1H)
IR(KBr) cm$^{-1}$: 3450, 3110, 1700, 1635, 1550, 1315, 1200, 975, 820, 685

EXAMPLE 12

Ethyl 6-(4-methoxycarbonylphenyl)-4-(4-oxo-2-thioxo-5-thiazolidinylidene)-5-hexenoate Yield 5%, m.p. 173.5°–176.7° C.
NMR(CDCl$_3$) δ: 9.34(br, s, 1H), 8.64(d, 1H), 8.05(d, 2H), 7.64(d, 2H), 7.12(d, 1H), 4.18(q, 4H), 3.93(s, 3H), 2.84(t, 2H), 2.60(t, 2H), 1.59(s, 3H), 1.28(t, 3H)
IR(KBr) cm$^{-1}$: 3214, 2980, 1720, 1705, 1611, 1554

EXAMPLE 13

Ethyl 6-(2-thienyl)-4-(4-oxo-2-thioxo-5-thiazolidinylidene)-5-hexenoate

Isomer A

Yield 5%, m.p. 157.9°–160.1° C.
NMR(CDCl$_3$) δ: 7.43–7.06(m, 4H), 6.43(d, 1H), 4.16(q, 2H), 3.37(t, 2H), 2.57(t, 2H), 1.27(t, 3H)
IR(KBr) cm$^{-1}$: 3134, 3034, 2980, 2866, 1730, 1679, 1589, 1546

Isomer B

Yield 4.5%, m.p. 151.4°–153.0° C.
NMR(CDCl$_3$) δ: 8.38(d, 1H), 7.40–7.03(m, 4H), 4.18(q, 2H), 2.70(t, 2H), 2.63(t, 2H), 1.28(t, 3H)
IR(KBr) cm$^{-1}$: 3150, 3054, 2924, 2862, 1733, 1680, 1589, 1549

EXAMPLE 14

Ethyl 6-(3-methyl-2-thienyl)-4-(4-oxo-2-thioxo-5-thiazolidinylidene)-5-hexenoate Isomer A Yield 4%
NMR(CDCl$_3$) δ: 7.46(d, 1H), 7.32(d, 1H), 6.89(d, 1H), 6.35(d, 1H), 4.14(q, 2H), 3.40(t, 2H), 2.57(t, 2H), 2.36(s, 3H), 1.26(t, 3H)

Isomer B

Yield 3%
NMR(CDCl$_3$) δ: 8.22(d, 1H), 7.29(d, 1H), 7.31(d, 1H), 6.87(d, 1H), 4.18(q, 2H), 2.82(t, 2H), 2.58(t, 2H), 2.35(s, 3H), 1.28(t, 3H)

EXAMPLE 15

Ethyl 4-[3-(4-oxo-2-thioxo-5-thiazolidinylidene)-1-butenyl]-methoxyphenoxyacetate Yield 50%
NMR(DMSO-d ) δ: 1.23(t, 3H), 2.16(s, 3H), 3.83(s, 3H), 4.18(q, 2H), 4.81(s, 2H), 6.93(d, 1H, J=8.3Hz), 7.15(d, 1H, J=8.3Hz), 7.17(s, 1H), 7.28(d, 1H, J=16Hz), 8.44(d, 1H, J=16Hz), 13.45(bs, 1H)

EXAMPLE 16

Ethyl 3-{4-[3-(4-oxo-2-thioxo-5-thiazolidinylidene)nonanyl]-phenyl}propionate

Isomer A

Yield 11%, m.p. 45.5°–47.7° C.
NMR(CDCl$_3$) δ: 0.90(t, 3H), 1.23(t, 3H), 1.2–1.6(8H), 2.43(dd, 2H), 2.59(t, 2H), 2.7–2.85(m, 4H), 2.93(t, 2H), 4.12(q, 2H), 7.12(q, 4H), 9.03(bs, 1H)
IR(KBr) cm$^{-1}$: 3430, 3160, 3070, 1730, 1700, 1610, 1450, 1220, 670

Isomer B

Yield 14%, m.p. 84.7°–87.3° C.
NMR(CDCl$_3$) δ: 0.90(t, 3H), 1.23(t, 3H), 1.2–1.45(6H), 1.45–1.6(2H), 2.15(dd, 2H), 2.60(t, 2H), 2.75(dd, 2H), 2.92(t, 2H), 3.06(dd, 2H), 4.12(q, 2H), 7.17(q, 4H), 9.22(bs, 1H)
IR(KBr) cm$^{-1}$: 3430, 3160, 3050, 1730, 1695, 1605, 1450, 1220, 1080, 675

EXAMPLE 17

5-[α-Methyl-4-(1H-tetrazol-5-yl)cinnamylidene)-4-oxo-2-thioxothiazolidine

Yield 10%, m.p. above 300° C.
Mass spectrum (m/e): 329 (M$^+$)
IR(KBr) cm$^{-1}$; 3400, 3036, 1684, 1616, 1550, 1437, 1204, 1075, 829

EXAMPLE 18

Methyl N-[2-(4-oxo-2-thioxo-5-thiazolidinylidene)propionyl]anthranilate

Yield 33%, m.p. 242° C. (dec.)
Mass spectrum (m/e): 336 (M$^-$)
NMR(CDCl$_3$+DMSO-d$_6$) δ: 2.80(s, 3H), 3.98(s, 3H), 7.21(t, 1H), 7.62(t, 1H), 8.11(d, 1H), 8.78(d, 1H), 12.16(s, 1H), 13.28(bs, 1H)
IR(KBr) cm$^{-1}$: 3460, 3174, 1691, 1659, 1607, 1592, 1541, 1440, 1301, 1281, 1092, 987, 929, 759

EXAMPLE 19

Methyl N-[5-(4-oxo-2-thioxo-5-thiazolidinylidene)hexanoyl]anthranilate

Yield 53%, m.p. 174°–178° C. (dec.)
Mass spectrum (m/e); 378 (M$^+$)
NMR(CDCl$_3$) δ: 1.90–2.10(m, 2H), 2.01(s, 3H), 2.54(t, 2H), 2.99(t, 2H), 3.92(s, 3H), 7.07(t, 1H), 7.54(t, 1H), 8.02(d, 1H), 8.71(d, 1H), 9.55(bs, 1H), 11.09(bs, 1H)
IR(KBr) cm$^{-1}$: 3260, 3116, 1701, 1670, 1648, 1611, 1591, 1540, 1454, 1379, 1268, 1252, 1211, 1090, 1069, 759

EXAMPLE 20

5-{4-[4-(1H-Tetrazol-5-yl)butyloxy]benzylidene}-4-oxo-2-thioxothiazolidine

Yield 39%, m.p. 225°–227° C. (dec.)
NMR(DMSO-d$_6$) δ: 1.70–2.00(m, 4H), 2.85–3.05(m, 2H), 4.00–4.20(m, 2H), 7.10(d, 2H), 7.56(d, 2H), 7.70(s, 1H), 13.80(bs, 1H), 15.90(bs, 1H)
IR(KBr) cm$^{-1}$: 2858, 1690, 1570, 1513, 1451, 1339, 1331, 1298, 944, 826

EXAMPLE 21

4-[3-(4-Oxo-2-thioxo-5-thiazolidinylidene)-1-butenyl]-phenoxy-acetic acid

A mixture of 0.12 g of Isomer A of ethyl 4-[3-(4-oxo-2-thioxo-5-thiazolidinylidene)-1-butenyl]phenoxyacetate, 5 ml of water and 1 ml of 5% sodium hydroxide solution was stirred at room temperature for one hour. 10% hydrochloric acid was added to the mixture and the precipitated crystals were collected by filtration and washed with methanol to give Isomer A (54% yield) of 4-[3-(4-oxo-2-thioxo-5-thiazolidinylidene)-1-butenyl]-phenoxyacetic acid.

In the same manner, Isomer B of 4-[3-(4-oxo-2-thioxo-5-thiazolidinylidene)-1-butenyl]phenoxyacetic acid was obtained in 47% yield from Isomer B of ethyl 4-[3-(4-oxo-2-thioxo-5-thiazolidinylidene)-1-butenyl]-phenoxyacetate.

Isomer A

Brown crystals, m.p. 260°-263° C. (dec.)
Mass spectrum (m/e): 335 (M+)
NMR(DMSO-d$_6$) δ: 2.50(s, 3H), 4.70(s, 2H), 6.65(d, 1H, J=16Hz), 6.95(d, 2H), 7.30(d, 1H, J=16Hz), 7.65(d, 2H), 13.30(br, s, 1H)
IR(KBr) cm$^{-1}$: 1753, 1674, 1599, 958

Isomer B

Brown crystals, m.p. 261°-263° C. (dec.)
Mass spectrum (m/e): 335 (M+)
NMR(DMSO-d ) δ: 2.15(s, 3H), 4.70(s, 2H), 7.00(d, 2H), 7.28(d, 1H, J=16Hz), 7.54(d, 2H), 8.45(d, 1H, J=16Hz), 13.40(br, s, 1H)
IR(KBr) cm$^{-1}$: 1740, 1699, 1603, 973

The ester products obtained in the above examples were subjected to hydrolysis by a similar procedure as in Example 21 to obtain the compounds shown in the following Examples 22 to 37.

EXAMPLE 22

6-(2-Fluorophenyl)-4-(4-oxo-2-thioxo-5-thiazolidinylidene)-5-hexenoic acid (from Isomer A of Example 5)

Yield 33%, m.p. 224°-227° C. (dec.)
NMR(CDCl$_3$ +DMSO) δ: 2.45-2.60, (m, 2H), 2.82(t, 2H), 7.00-7.40(m, 4H), 7.70(t, 1H), 8.63(d, 1H, J=16.6Hz), 13.20(bs, 1H)
IR(KBr) cm$^{-1}$: 3414, 1712, 1662, 1607, 1555, 1485, 1454, 1286, 1240, 1210, 1194, 969, 762

EXAMPLE 23

6-(4-Trifluoromethylphenyl)-4-(4-oxo-2-thioxo-5-thiazolidinylidene)-5-hexenoic acid (from Isomer A of Example 6)

Yield 31%, m.p. 182°-188° C. (dec.)
IR(KBr) cm$^{-1}$: 3412, 1716, 1690, 1674, 1617, 1554, 1329, 1200, 1133, 1069, 977, 827

EXAMPLE 24

6-(4-Cyanophenyl)-4-(4-oxo-2-thioxo-5-thiazolidinylidene)-5-hexenoic acid (from the product of Example 7)

Yield 76% (cis-trans mixture)
m.p. 248°-251° C. (dec.)
IR(KBr) cm$^{-1}$: 3406, 2232, 1735, 1674, 1548, 1436, 1293, 1212, 1134, 1070, 825

EXAMPLE 25

6-(3-Hydroxyphenyl)-4-(4-oxo-2-thioxo-5-thiazolidinylidene)-5-hexenoic acid (from Isomer A of Example 8)

Yield 80%, m.p. 248°-250° C. (dec.)
NMR(DMSO-d$_6$) δ: 2.20-2.70(m, 4H), 6.50-7.20(m, 5H), 8.72(d, 1H, J=16Hz), 9.50(bs, 1H)
IR(KBr) cm$^{-1}$: 3336, 1681, 1608, 1547, 1450, 1204, 953

EXAMPLE 26

4-[3-(4-Oxo-2-thioxo-5-thiazolidinylidene)-1-nonenyl]-benzoic acid (from Isomers A and B of Example 9)

Isomer A (from Isomer A of Example 9)

Yield 80%, m.p. 228°-230° C. (dec.)
Mass spectrum (m/e): 375 (M+)
NMR(CDCl$_3$-DMSO-d$_6$) δ: 0.80-1.00(m, 3H), 1.20-1.70(m, 8H), 3.00-3.20(m, 2H), 6.74(d, 1H, J=15.6Hz), 7.18(d, 1H, J=15.6Hz), 7.60(d, 2H), 8.04(d, 2H), 13.09(bs, 1H
IR(KBr) cm$^{-1}$: 1693, 1611, 1547, 1420, 1204, 1073, 948, 767

Isomer B (from Isomer B of Example 9)

Yield 40%, m.p. 240°-243° C. (dec.)
Mass spectrum (m/e); 375 (M+)
NMR (CDCl$_3$ - DMSO-d$_6$) δ: 0.80-1.00(m, 3H), 1.20-1.70(m, 8H), 2.49(t, 2H), 7.06(d, 1H, J=16.6Hz), 7.62(d, 2H), 8.04(d, 2H), 8.71(d, 1H, J=16.6Hz), 12.65(bs, 1H)
IR(KBr) cm$^{-1}$: 3430, 1696, 1610, 1546, 1441, 1420, 1267, 2203,

EXAMPLE 27

2-[3-(4-Oxo-2-thioxo-5-thiazolidinylidene)hexyl]-phenoxyacetic acid (from Isomers A and B of Example 10)

Isomer A (from Isomer A of Example 10)

Yield 95%, m.p. 181.5°-184.5° C.
NMR(CDCl$_3$+CD$_3$OD) δ: 1.00(t, 3H), 1.57(m, 2H), 2.52(m, 2H), 2.75-2.95(m, 4H), 4.67(s, 2H), 6.73(d, 1H), 6.93(t, 1H), 7.05-7.27(2H)
IR(KBr) cm$^{-1}$: 3440, 3150, 3060, 1745, 1650, 1595, 1497, 1235, 755

Isomer B (from Isomer B of Example 10)

Yield 95%, m.p. 219.5°-222.5° C.
NMR(CDCl$_3$+CD$_3$OD) δ: 0.97(t, 3H), 1.60(m, 2H), 2.19(m, 2H), 2.88(m, 2H), 3.09(m, 2H), 4.64(s, 2H), 6.76(d, 1H), 6.94(t, 1H), 7.10-7.27(2H)
IR(KBr) cm$^{-1}$: 3430, 3160, 3060, 1740, 1690, 1595, 1500, 1440, 1220, 750, 675

EXAMPLE 28

4-[3-(4-Oxo-2-thioxo-5-thiazolidinylidene)-1-nonenyl]-cinnamic acid (from Isomer A of Example 11)

Yield 90%, m.p. 230°-243° C.
IR(KBr) cm$^{-1}$: 3450, 1690, 1630, 1550, 1430, 1200, 980

EXAMPLE 29

6-(4-Carboxyphenyl)-4-(4-oxo-2-thioxo-5-thiazolidinylidene)-5-hexenoic acid (from the product of Example 12)

Yield 70%, m.p. 263° C. (dec.)
IR(KBr) cm$^{-1}$: 3400, 3075, 2850, 1695, 1611, 1545

EXAMPLE 30

6-(2-Thienyl)-4-(4-oxo-2-thioxo-5-thiazolidinylidene)-5-hexenoic acid (from the product of Example 13)

Yield 90%, m.p. 175° C. (dec.)
IR(KBr) cm$^{-1}$: 3412, 2850, 1682, 1591, 1549

EXAMPLE 31

6-(3-Methyl-2-thienyl)-4-(4-oxo-2-thioxo-5-thiazolidinylidene)-5-hexenoic acid (from the product of Example 14)

Yield 87%, m.p. 207° C. (dec.)
IR(KBr) cm$^{-1}$: 3430, 2850, 1700, 1585, 1551

EXAMPLE 32

4-[3-(4-Oxo-2-thioxo-5-thiazolidinylidene)-1-butenyl]-2-methoxyphenoxyacetic acid (from the product of Example 15)

NMR(DMSO-d$_6$) δ: 2.15(s, 3H), 3.83(s, 3H), 4.71(s, 2H), 6.91(d, 1H), 7.10–7.20(m, 2H), 7.26(d, 1H, J=16.6Hz), 8.44(d, 1H, J=16.6Hz), 13.30(bs, 2H)
IR(KBr) cm$^{-1}$: 3500, 1744, 1667, 1599, 1582, 1549, 1517, 1312, 1146, 1075, 1031, 966, 825, 676

EXAMPLE 33

3-{4-[3-(4-Oxo-2-thioxo-5-thiazolidinylidene)nonanyl]phenyl}propionic acid (from Isomers A and B of Example 16)

Isomer A (from Isomer A of Example 16)

Yield 90%, m.p. 96.4°–100.5° C.
NMR(CDCl$_3$) δ: 0.90(t, 3H), 1.2–1.6(8H), 2.45(dd, 2H), 2.66(t, 2H), 2.7–2.9(m, 4H), 2.94(t, 2H), 7.12(q, 4H), 9.78(bs, 1H)
IR(KBr) cm$^{-1}$: 3430, 3140, 3050, 1715, 1665, 1605, 1450, 1325, 1225, 830, 680

Isomer B (from Isomer B of Example 16)

Yield 95%, m.p. 153.5°–157.0° C.
NMR(CDCl$_3$)δ: 0.90(t,3H), 1.2–1.4(6H), 1.4–1.6(2H), 2.17(dd,2H), 2.6–2.8(m,4H), 2.95(t,2H), 3.06(dd,2H), 7.18(q,4H), 9.98(bs,1H)
IR(KBr)cm$^{-1}$: 3430, 3175, 3075, 1710, 1690, 1440, 1300, 1220, 1080, 670

EXAMPLE 34

3-{2-[3-(4-Oxo-2-thioxo-5-thiazolidinylidene)pentyl]pyrrol-1-yl}propionic acid (from butyl 3-{2-[3-(4-oxy-2-thioxo-5-thiazolidinylidene)pentyl]pyrrol-1-yl}propionate)

Yield 82%, m.p. 176.5° C.
IR(KBr)cm$^{-1}$: 3430, 3075, 1720, 1695, 1610, 1450, 1215, 1085, 730, 660.

EXAMPLE 35

6-(2-Furyl)-4-(4-oxo-2-thioxo-5-thiazolidinylidene)-5-hexenoic acid (from ethyl 6-(2-furyl)-4-(4-oxo-2-thioxo-5-thiazolidinylidene)-5-hexenoate)

Yield 80%, m.p. above 310° C.
IR(KBr) cm$^{-1}$: 3410, 2970, 2850, 1660, 1640, 1600, 1550

EXAMPLE 36

N-[2-(4-Oxo-2-thioxo-5-thiazolidinylidene)propionyl]anthranilic acid (from the product of Example 18)

Yield 34%, m.p. 257° C. (dec.)
Mass spectrum (m/e); 322 (M$^+$)
NMR(CDCl$_3$+DMSO-d$_6$) δ: 2.77(s, 3H), 7.19(t, 1H), 7.59(t, 1H), 8.13(d, 1H), 8.77(d, 1H), 12.55(s, 1H), 13.28(bs, 1H)
IR(KBr) cm$^{-1}$: 3158, 1691, 1659, 1605, 1592, 1540, 1456, 1302, 1251, 1172, 987, 931, 758

EXAMPLE 37

N-[5-(4-Oxo-2-thioxo-5-thiazolidinylidene)hexanoyl]anthranilic acid (from the product of Example 19)

Yield 80%, m.p. 206°–212° C. (dec.)
Mass spectrum (m/e); 346 (M$^+$)
IR(KBr) cm$^{-1}$: 3074, 1713, 1664, 1608, 1586, 1533, 1449, 1411, 1294, 1261, 1203, 1164, 1151, 1079, 755

EXAMPLE 38

7-(3,4-Dimethoxyphenyl)-5-(4-oxo-2-thioxo-5-thiazolidinylidene)-6-heptenoic acid A mixture of 1.60 g (0.012 mol) of rhodanine, 3.06 g (0.01 mol) of ethyl 7-(3,4-dimethoxyphenyl)-5-oxo-6-heptenoate, 0.77 g (0.01 mol) of ammonium acetate and 20 ml of toluene was heated under reflux for 8 hours. After cooling, 100 ml of water were added to the reaction mixture d with ethyl acetate (3×100 ml). The ethyl acetate layer was washed three times with water and once with a saturated saline solution, dried over magnesium sulfate, filtered and the filtrate was concentrated under reduced pressure to afford a reddish brown oily substance. The oily substance was purified by silica gel column chromatography (eluent, chloroform) to obtain 0.5 g of ethyl 7-(3,4-dimethoxyphenyl)-5-(4-oxo-2-thioxo-5-thiazolidinylidene)-6-heptenoate. To 0.21 g of this compound was added 5 ml of water and 1 ml of 5% sodium hydroxide solution and the mixture was stirred at room temperature for 3 hours. This mixture was acidified with 10% hydrochloric acid, 100 ml of water was added to the acidified mixture which was extracted with ethyl acetate (3 ×120 ml). The ethyl acetate layer was washed three times with water and once with saturated saline solution, dried over magnesium sulfate, filtered and the filtrate was concentrated under reduced pressure. The residue was purified by silica gel column chromatography (eluent, chloroform : methanol TM 10:1) to obtain 0.12 g of Isomer A of 7-(3,4-dimethoxyphenyl)-5-(4-oxo-2-thioxo-5-thiazolidinylidene)-6-heptenoic acid from the first eluate and 0.03 g of Isomer B from the subsequent eluate.

Ethyl ester

Reddish brown crystals, m.p. 146°–148° C. (dec.)
Mass spectrum (m/e); 421 (M$^+$)
IR(KBr) cm$^{-1}$: 1714, 1671, 1596, 1577, 971

Isomer A

Reddish brown crystals, m.p. 223°–225° C. (dec.)
Mass spectrum (m/e); 393 (M$^+$)
NMR(DMSO-d$_6$) δ: 1.80–2.00(m, 2H), 2.40–2.50(m, 2H), 2.52–2.70(m, 2H), 3.91(s, 3H), 3.93(s, 3H), 6.89(d, 1H), 7.10–7.20(m, 3H), 8.01(d, 1H, J=16Hz), 13.00(br, s, 1H)
IR(KBr) cm$^{-1}$: 1697, 1596, 1541, 972

Isomer B

Reddish brown crystals. m.p. 178°–180° C. (dec.)
Mass spectrum (m/e): 393 (M⁻)
NMR(DMSOd₆) δ: 1.80–2.00(m, 2H), 2.35–2.50(m, 2H), 3.05–3.25(m, 2H), 3.91(s, 3H), 3.93(s, 3H), 6.50(d, 1H, J=16Hz), 6.80–6.95(m, 1H), 7.00–7.20(m, 2H), 7.28(d, 1H, J=16Hz), 12.30(br, s, 1H)
IR(KBr) cm⁻¹: 1704, 1595, 1540, 954

EXAMPLE 39

Ethyl 2-[3-(4-oxo-2-thioxo-5-thiazolinylidene)-1-butenyl]-phenoxacetate

A mixture of 1.33 g (0.01 mol) of rhodanine, 2.48 g (0.01 mol) of ethyl 2-(3-oxo-1-butenyl]phenoxyacetate, 0.77 g (0.01 mol) of ammonium acetate and 20 ml of toluene was heated under reflux for 3 hours. After cooling, 100 ml of water were added to the reaction mixture which was extracted with ethyl acetate (3×100 ml). The ethyl acetate layer was washed twice with water and once with a saturated saline solution, dried and concentrated under reduced pressure to give orange crystals. The crystals were purified by silica gel column chromatography (eluent, chloroform : ethyl acetate) to obtain ethyl 2-[3-(4-oxo-2-thioxo-5-thiazolinylidene)-1-butenyl]phenoxyacetate (35.8% yield) from the first eluate.

In accordance with similar procedure as mentioned in Example 39, the compounds shown in the following Examples 40 to 66 were obtained from the corresponding aldehydes or ketones.

EXAMPLE 40

Methyl 2-[3-(4-oxo-2-thioxo-5-thiazolinylidene)-1-butenyl]-phenoxyacetate

Yield 27.0%
Reddish brown crystals, m.p. 213°–215° C. (dec.)
IR(KBr) cm⁻¹: 1749, 1662, 1433, 1205
NMR(DMSOd₆) δ: 2.16(s, 3H), 3.71(s, 3H), 4.90(s, 2H), 6.98(d, 1H), 7.08(d, 1H), 7.34(t, 1H), 7.52–7.62(3H), 8.57(d, 1H), 13,49(br, s, 1H)

EXAMPLE 41

Methyl 2-[2-methyl-3-(4-oxo-2-thioxo-5-thiazolinylidene)-1-propenyl]phenoxyacetate Yield 50.0%
Orange crystals, m.p. 164°–166° C. (dec.)
IR(KBr) cm⁻¹: 1748, 1696, 1568, 1446, 1308, 1240, 1213
NMR(CDCl₃) δ: 2.17(s, 3H), 3.82(s, 3H), 4.70(s, 2H), 6.79(d, 1H), 7.03(t, 1H), 7.27–7.34(3H), 7.52(s, 1H), 10.08(br, s, 1H)

EXAMPLE 42

Methyl 2-methoxy-4-[3-(4-oxo-2-thioxo-5-thiazolinylidene)-1-butenyl]phenoxyacetate Yield 37.9%
Orange crystals, m.p. 232°–234° C. (dec.)
IR(KBr) cm⁻¹: 1733, 1663, 1511, 1214, 677
NMR(DMSO-d₆) δ: 2.16(s, 3H), 3.71(s, 3H), 3.83(s, 3H), 4.83(s, 2H), 6.94(d, 1H), 7.12–7.32(3H), 8.44(d, 1H), 13.45(br, s, 1H)

EXAMPLE 43

Ethyl 2-methoxy-4-[3-(4-oxo-2-thioxo-5-thiazolinylidene)-butyl]phenoxyacetate

Yield 23.3%
Pale yellow needles. m.p. 123°–126° C.
IR(KBr) cm⁻¹: 1773, 1688, 1607, 1517, 1436, 1238, 1195, 806
NMR(CDCl₃) δ: 1.29(t, 3H), 1.95(s, 3H), 2.76(t, 2H), 3.14(t, 2H), 3.88(s, 3H), 4.26(q, 2H), 4.66(s, 2H), 6.75(s, 2H), 6.81(s, 1H), 9.89(br, s, 1H)

EXAMPLE 44

Methyl 2-ethoxy-4-[3-(4-oxo-2-thioxo-5-thiazolinylidene)-1-butenyl]phenoxyacetate Yield 31.3%
Orange crystals, m.p. 213.5° C.
IR(KBr) cm⁻¹: 1740, 1675, 1550, 1207, 968
NMR(DMSOd₆) δ: 1.36(t, 3H), 2.17(s, 3H), 3.70(s, 3H), 4.10(q, 2H), 4.83(s, 2H), 6.93(d, 1H), 7.14(d, 1H), 7.17(s, 1H), 7.25(d, 1H), 8.43(d, 1H), 13.30(br, s, 1H)

EXAMPLE 45

Methyl 2-ethoxy-4-[3-(4-oxo-2-thioxo-5-thiazolinylidene)butyl]-phenoxyacetate

Yield 76.0%
Yellow crystals, m.p. 107° C.
IR(KBr) cm⁻¹: 1738, 1700, 1602, 1522, 1457, 1223

EXAMPLE 46

Methyl 2-methoxy-6-(3-(4-oxo-2-thioxo-5-thiazolinylidene)-1-butenyl]phenoxyacetate Yield 38.2%
Orange crystals, m.p. 227° C. (dec.)
IR(KBr) cm⁻¹: 1740, 1662, 1553, 1280, 1207

EXAMPLE 47

Methyl 2-methoxy-6-[3-(4-oxo-2-thioxo-5-thiazolinylidene)-butyl]phenoxyacetate

Yield 40.0%
Yellow crystals, m.p. 150°–167° C.
IR(KBr) cm⁻¹: 1782, 1740, 1698, 1602, 1215, 663

EXAMPLE 48

Methyl 2,6-dimethoxy-4-[3-(4-oxo-2-thioxo-5-thiazolinylidene)-1-butenyl]phenoxyacetate Yield 2.0%
Orange crystals, m.p. 222° C.
IR(KBr) cm⁻¹: 3460, 1675, 1583, 1455, 1215, 1135

EXAMPLE 49

Methyl 4-chloro-2-[3-(4-oxo-2-thioxo-5-thiazolinylidene)-1-butenyl]phenoxyacetate Yield 19.6%
Orange crystals, m.p. 225°–226° C.
IR(KBr) cm⁻¹: 1760, 1678, 1553, 1440, 1214

NMR(DMSO-d$_6$) δ: 2.15(s, 3H), 3.70(s, 3H), 4.92(s, 2H), 7.02(d, 1H), 7.30-7.58(m, 3H), 8.58(d, 1H), 13.49(br, s, 1H)

EXAMPLE 50

Benzyl 4-chloro-2-[3-(4-oxo-2-thioxo-5-thiazolinylidene)-1-butenyl]phenoxyacetate Yield 12.5%
Orange crystals, m.p. 130°-140° C.
IR(KBr) cm$^{-1}$: 1748, 1677, 1554, 1444, 1203

EXAMPLE 51

Butyl 4-chloro-2-[3-(4-oxo-2-thioxo-5-thiazolinylidene)-1-butenyl]phenoxyacetate Isomer A Yield 5.8%
Orange crystals, m.p. 189°-190° C.
IR(KBr) cm$^{-1}$: 3440, 1750, 1685, 1555, 1210
NMR(CDCl$_3$) δ: 0.92(t, 3H), 1.30-1.49(m, 2H), 1.58-1.74(m, 2H), 2.60(s, 3H), 4.25(t, 2H), 4.71(s, 2H), 6.73(d, 1H), 6.82(d, 1H), 7.30(m, 1H), 7.50(s, 1H), 7.55(d, 1H), 9.42(br, s, 1H)

Isomer B

Yield 6.8%
Orange crystals, m.p. 149°-150° C.
IR(KBr) cm$^{-1}$: 3440, 1748, 1680, 1550, 1205
NMR(CDCl$_3$) δ: 0.93(t, 3H), 1.28-1.48(m, 2H), 1.56-1.74(m, 2H), 2.21(s, 3H), 4.22(t, 2H), 4.70(s, 2H), 6.70(d, 1H), 7.25(m, 1H), 7.50-7.70(2H), 8.60(d, 1H), 9.42(br, s, 1H)

EXAMPLE 52

1-{4-Chloro-2-[3-(4-oxo-2-thioxo-5-thiazolinylidene)-1-butenyl]phenoxyacetyl}piperidine Yield 11.5%
Orange crystals, m.p. 275° C.
IR(KBr) cm$^{-1}$: 2950, 2860, 1705, 1650, 1490, 1450, 1230, 1195
NMR(DMSOd$_6$) δ: 1.40-1.70(m, 6H), 2.17(s, 3H), 3.30-3.50(m, 4H), 4.97(s, 2H), 7.00(d, 1H), 7.30-7.45(2H) 7.52(s, 1H), 8.57(d, 1H), 13.50(br, s, 1H)

EXAMPLE 53

Ethyl 2-methoxy-4-[2-methyl-3-(4-oxo-2-thioxo-5-thiazolinylidene)-1-propenyl]phenoxyacetate Yield 24.7%
Brown crystals, m.p. 179°-181° C. (dec.)
IR(KBr) cm$^{-1}$: 1757, 1688, 1553, 1516, 1445, 1265, 1193, 1147
NMR(DMSO-d$_6$) δ: 1.22(t, 3H), 2.19(s, 3H), 3.82(s, 3H), 4.18(q, 2H), 4.81(s, 2H), 6.90-7.19(m, 4H), 7.35(s, 1H), 13.68(br, s, 1H)

EXAMPLE 54

Ethyl 2,6-diisopropyl-4-[3-(4-oxo-2-thioxo-5-thiazolinylidene)-1-butenyl]phenoxyacetate Yield 11.6%
Yellow crystals, m.p. 239°-241° C. (dec.)
IR(KBr) cm$^{-1}$: 1754, 1674, 1455, 1215, 1201
NMR(CDCl$_3$) δ: 1.27(d, 12H), 1.35(t, 3H), 2.20(s, 3H), 3.28-3.42(m, 2H), 4.32(q, 2H), 4.39(s, 2H), 7.11(d, 1H), 7.33(s, 2H), 8.58(d, 1H), 9.79(br, s, 1H)

EXAMPLE 55

Ethyl 2-methoxy-4-[3-(3-methyl-4-oxo-2-thioxo-5-thiazolinylidene)-1-butenyl]phenoxyacetate Isomer A Yield 9.1%
Yellow crystals, m.p. 183°-187° C.
IR(KBr) cm$^{-1}$: 1731, 1695, 1562, 1517, 1303, 1280, 1250, 1143, 1122
NMR(CDCl$_3$) δ: 1.30(t, 3H), 2.64(s, 3H), 3.48(s, 3H), 3.95(s, 3H), 4.28(q, 2H), 4.73(s, 2H), 6.65(d, 1H), 6.80(d, 1H), 7.05-7.17(3H)

Isomer B

Yield 9.5%
Orange crystals, m.p. 172°-174° C. (dec.)
IR(KBr) cm$^{-1}$: 1739, 1511, 1279, 1127, 803
NMR(CDCl$_3$) δ: 1.29(t, 3H), 2.21(s, 3H), 3.48(s, 3H), 3.96(s, 3H), 4.27(q, 2H), 4.72(s, 2H), 6.79(d, 1H), 7 03-7.11(3H), 8.62(d, 1H)

EXAMPLE 56

Methyl 4-bromo-2-[3-(4-oxo-2-thioxo-5-thiazolinylidene)-1-butenyl]phenoxyacetate Yield 20.8%
Orange crystals, m.p. 235° C.
IR(KBr) cm$^{-1}$: 1763, 1678, 1442, 1215, 680
NMR(DMSOd$_6$) δ: 2.17(s, 3H), 3.74(s, 3H), 4.90(s, 2H), 6.95(d, 1H), 7.40-7.70(3H), 8.58(d, 1H), 13.46(br, s, 1H)

EXAMPLE 57

Methyl 2,4-dichloro-6-[3-(4-oxo-2-thioxo-5-thizolinylidene)-1-butenyl]phenoxyacetate Yield 40.7%
Yellow crystals, m.p. 252° C.
IR(KBr) cm$^{-1}$: 1765, 1450, 1205, 1175, 1050
NMR(DMSOd$_6$) δ: 2.20(s, 3H), 3.75(s, 3H), 4.72(s, 2H), 7.57(q, 2H), 7.64(d, 1H), 8.55(d, 1H), 13.50(br, s, 1H)

EXAMPLE 58

Methyl 2,4-dibromo-6-[3-(4-oxo-2-thioxo-5-thiazolinylidene)-1-butenyl]phenoxyacetate Yield 46.3%
Yellow crystals, m.p. 249° C.
IR(KBr) cm$^{-1}$: 1765, 1710, 1560, 1448, 1202
NMR(DMSOd$_6$) δ: 2.18(s, 3H), 3.75(s, 3H), 4.67(s, 2H), 7.50(d, 1H), 7.77(dd, 2H), 8.55(d, 1H), 13.50(br, s, 1H)

EXAMPLE 59

Methyl 2-methoxy-5-[3-(4-oxo-2-thioxo-5-thiazolinylidene)-1-butenyl]phenoxyacetate Yield 37.8%
Red powders, m.p. 225°-229° C. (dec.)
IR(KBr) cm$^{-1}$: 1745, 1675, 1546, 1514, 1266, 1218, 677

NMR(DMSOd₆) δ: 2.52(s, 3H), 3.73(s, 3H), 3.83(s, 3H), 4.88(s, 2H), 6.63(d, 1H), 7.02(d, 1H), 7.26–7.33(3H), 3.39(br. s, 1H)

EXAMPLE 60

Methyl 2-methoxycarbonylmethoxy-4-[3-(4-oxo-2-thioxo-5-thiazolinylidene)-1-butenyl]phenoxyacetate Yield 10.4%
Orange crystals, m.p. 190°–196° C.
IR(KBr) cm⁻¹: 1750, 1682, 1550, 1517, 1440, 1218, 685
NMR(DMSO-d₆) δ: 2.54(s, 3H), 3.75(s, 3H), 3.77(s, 3H), 4.85(s, 2H), 4.90(s, 2H), 6.64(d, 1H), 6.95(d, 1H), 7.10–7.30(m, 3H), 13.30(br, s, 1H)

Isomer B

Yield 17.8%
Red crystals, m.p. 182°–186° C.
IR(KBr) cm⁻¹: 1765, 1670, 1545, 1517, 1435, 1220, 677
NMR(DMSO-d₆) δ: 2.17(s, 3H), 3.75(s, 3H), 3.77(s, 3H), 4.83(s, 2H), 4.85(s, 2H), 6.95(d, 1H), 7.10–7.30(m, 3H), 8.45(d, 1H), 13.50(br, s, 1H)

EXAMPLE 61

Methyl 2-(2-propyl-3-(4-oxo-2-thioxo-5-thiazolinylidene)-1-propenyl]phenoxyacetate

Isomer A

Yield 13.5%
Yellow crystals, m.p. 147°–149° C. (dec.)
IR(KBr) cm⁻¹: 1743, 1699, 1580, 1432, 1227, 749
NMR(CDCl₃) δ: 1.03(t, 3H), 1.50–1.68(m, 2H), 2.44(t, 2H), 3.80(s, 3H), 4.68(s, 2H), 6.78(d, 1H), 7.01(t, 1H), 7.15–7.34(3H), 7.63(s, 1H), 9.88(br. s, 1H)

Isomer B

Yield 17.5%
Brown crystals, m.p. 142°–144° C. (dec.)
IR(KBr) cm⁻¹: 1772, 1687, 1557, 1437, 1215, 1187
NMR(CDCl₃) δ: 0.99(t, 3H), 1.15–1.62(m, 2H), 2.40–2.48(m, 2H), 3.81(s, 3H), 4.71(s, 2H), 6.79(d, 1H), 7.03(t, 1H), 7.27–7.38(m, 2H), 7.47(s, 1H), 10.12(br, s, 1H)

EXAMPLE 62

Methyl 4-isopropyl-2-[3-(4-oxo-2-thioxo-5-thiazolinylidene)-1-butenyl]phenoxyacetate

Isomer A

Yield 24.6%
Orange crystals, m.p. 200°–202° C.
IR(KBr) cm⁻¹: 1760, 1673, 1204, 676
NMR(CDCl₃) δ: 1.26(d, 6H), 2.22(s, 3H), 2.85–2.99(m, 1H), 3.81(s, 3H), 4.72(s, 2H), 6.70(d, 1H), 7.15(dd, 1H), 7.56–7.70(3H), 8.65(d, 1H), 10.63(br, s, 1H).

Isomer B

Yield 9.6%
Orange powders, m.p. 192°–196° C. (dec.)
IR(KBr) cm⁻¹: 1759, 1679, 1547, 1210, 678
NMR(CDCl₃) δ: 1.25(d, 6H), 2.62(s, 3H), 2.82–2.96(m, 1H), 3.84(s, 3H), 4.73(s, 2H), 6.72(d, 1H), 6.89(d, 1H), 7.18(dd, 1H), 7.35(1H), 7.59(d, 1H), 9.65(br, s, 1H)

EXAMPLE 63

Methyl 2-[2-methyl-3-(4-oxo-2-thioxo-5-thiazolinylidene)-1-propenyl]phenoxyacetate Yield 41.5%
Yellowish brown powders, m.p. 160°–162° C. (dec.)
IR(KBr) cm⁻¹: 1763, 1732, 1691, 1564, 1437, 1205, 1190, 679
NMR(DMSOd₆) δ: 2.15(s, 3H), 3.72(s, 3H), 4.82(s, 2H), 6.91–7.38(6H), 13.73(br. s, 1H)

EXAMPLE 64

Methyl 2,6-dimethyl-4-[3-(4-oxo-2-thioxo-5-thiazolinylidene)-1-butenyl]phenoxyacetate Yield 41.0%
Yellow crystals, m.p. 211°–214° C. (dec.)
IR(KBr) cm⁻¹: 1760, 1717, 1557, 1440, 1218, 1206, 1153

EXAMPLE 65

Methyl 4-methoxy-2-[3-(4-oxo-2-thioxo-5-thiazolinylidene)-1-butenyl]phenoxyacetate Yield 45.7%
Red crystals, m.p. 244°–247° C. (dec.)
IR(KBr) cm⁻¹: 1746, 1497, 1216, 1200
NMR(DMSO-d₆) δ: 2.16(s, 3H), 3.70(s, 3H), 3.76(s, 3H), 4.83(s, 2H), 6.88–7.08(3H), 7.52(d, 1H), 8.54(d, 1H), 13.48(br, s, 1H)

EXAMPLE 66

Methyl 4-trifluoromethyl-2-[3-(4-oxo-2-thioxo-5-thiazolinylidene)-1-butenyl]phenoxyacetate Yield 38.3%
m.p. 240°–241° C. (dec.)
IR(KBr) cm⁻¹: 3272, 1734, 1429, 1221, 1190, 1131, 1107
NMR(DMSO-d₆) δ: 2.17(s, 3H), 3.73(s, 3H), 5.05(s, 2H), 7.21(d, 1H), 7.49(d, 1H), 7.67(d, 1H), 7.83(s, 1H), 8.65(d, 1H), 13.56(br, s, 1H)

EXAMPLE 67

2-[3-(4-Oxo-2-thioxo-5-thiazolinylidene)-1-butenyl]-phenoxyacetic acid

A mixture of 0.85 g of ethyl 2-[3-(4-oxo-2-thioxo-5-thiazolinylidene)-1-butenyl]phenoxyacetate, 5 ml of water and 1 ml of 5% sodium hydroxide solution was stirred at room temperature for one hour. 10% hydrochloric acid was added to the mixture and the precipitated crystals were collected by filtration and washed with methanol to give 2-[3-(4-oxo-2thioxo-5-thiazolinylidene)-1-butenyl]phenoxyacetic acid in the yield of 76%.
Yellowish brown crystals, m.p. 235°–238° C. (dec.)
IR(KBr) cm⁻¹: 3398, 1738, 1672, 1549, 1438, 1244, 1217, 751, 670
NMR(DMSOd₆) δ: 2.20(s, 3H), 4.69(s, 2H), 6.82(d, 1H), 7.03(t, 1H), 7.29(t, 1H), 7.56–7.71(m, 2H), 8.64(d, 1H), 13.05(br, s, 1H)

The ester products obtained in the above examples were subjected to hydrolysis by a similar procedure as in Example 67 to obtain the compounds shown in the following Examples 68 to 89.

EXAMPLE 68

2-[2-Methyl-3-(4-oxo-2-thioxo-5-thiazolinylidene)-1-propenyl]phenoxyacetic acid (from the product of Example 41)

Yield 21.0%
Orange crystals. m.p. 218°–220° C. (dec.)
IR(KBr) cm$^{-1}$: 3432, 1719, 1595, 1568, 1455, 1236, 1194, 743
NMR(DMSOd$_6$) δ: 2.08(s, 3H), 4.70(s, 2H), 6.95(d, 1H), 6.98(d, 1H), 7.13(s, 1H), 7.15(s, 1H), 7.25–7.34(2H)

EXAMPLE 69

2-Methoxy-4-[3-(4-oxo-2-thioxo-5-thiazolinylidene)-butyl]-phenoxyacetic acid (from the product of Example 43)

Yield 32.7%
Yellow powders. m.p. 166°–170° C. (dec.)
IR(KBr) cm$^{-1}$: 1724, 1690, 1608, 1517, 1240, 1206, 816

EXAMPLE 70

2-Ethoxy-4-[3-(4-oxo-2-thioxo-5-thiazolinylidene)-1-butyl]phenoxyacetic acid (from the product of Example 44)

Yield 99.8%
Red crystals. m.p. 249°–250° C.
IR(KBr) cm$^{-1}$: 3460, 1739, 1675, 1555, 1523, 1218
NMR(DMSO-d$_6$) δ: 1.40(t, 3H), 2.16(s, 3H), 4.10(q, 2H), 4.72(s, 2H), 6.88(d, 1H), 7.10–7.30(m, 3H), 8.45(d, 1H)

EXAMPLE 71

2-Ethoxy-4-[3-(4-oxo-2-thioxo-5-thiazolinylidene)-butyl]phenoxyacetic acid (from the product of Example 45)

Yield 81.5%
Yellow crystals. m.p. 199°–200° C.
IR(KBr) cm$^{-1}$: 3410, 1715, 1610, 1520, 1215

EXAMPLE 72

2-Methoxy-6-[3-(4-oxo-2-thioxo-5-thiazolinylidene)-1-butenyl] phenoxyacetic acid (from the product of Example 46)

Yield 83.0%
Yellowish brown crystals, m.p. 210° C. (dec.)
IR(KBr) cm$^{-1}$: 3425 1690, 1608, 1580, 1274, 1210

EXAMPLE 73

2-Methoxy-6-(3-(4-oxo-2-thioxo-5-thiazolinylidene)-butyl]phenoxyacetic acid (from the product of Example 47)

Yield 95%
Yellow crystals, m.p. 209°–229° C.
IR(KBr) cm$^{-1}$: 3450, 1698, 1610, 1485, 1220

EXAMPLE 74

2,6-Dimethoxy-4-[3-(4-oxo-2-thioxo-5-thiazolinylidene)-1-butenyl]phenoxyacetic acid (from the product of Example 48)

Yield 83.0%
Light brown crystals, m.p. 227°–237° C.
IR(KBr) cm$^{-1}$: 3450, 1680, 1585, 1425, 1215, 1122

EXAMPLE 75

4-Chloro-2-[3-(4-oxo-2-thioxo-5-thiazolinylidene)-1-butenyl]phenoxyacetic acid (from the product of Example 49)

Yield 95.5%
Red crystals. m.p. 244°–247° C.
IR(KBr) cm$^{-1}$: 3460, 1685, 1601, 1545, 1200

EXAMPLE 76

2-Methoxy-4-[2-methyl-3-(4-oxo-2-thioxo-5-thiazolinylidene)-1-propenyl]phenoxyacetic acid (from the product of Example 53)

Yield 15.7%
Brown crystals, m.p. 229°–231° C. (dec.)
IR(KBr) cm$^{-1}$: 3390, 1737, 1569, 1511, 1276, 1233, 1194, 686
NMR(DMSOd$_6$) δ: 2.20(s, 3H), 3.81(s, 3H), 4.72(s, 2H), 6.88–7.18(4H), 7.35(s, 1H), 13.00(br, s, 1H), 13.68(br, s, 1H)

EXAMPLE 77

2,6-Diisopropyl-4-[3-(4-oxo-2-thioxo-5-thiazolinylidene)-1-butenyl]phenoxyacetic acid (from the product of Example 54)

Yield 32.9%
Yellow crystals. m.p. 279°–282° C.
IR(KBr) cm$^{-1}$: 3410, 2964, 1673, 1219
NMR(DMSOd$_6$) δ: 1.21(d, 12H), 2.17(s, 3H), 3.24–3.34(m, 2H), 4.35(s, 2H), 7.32(d, 1H), 7.37(s, 2H), 8.50(d, 1H), 13.47(br, s, 1H)

EXAMPLE 78

2-Methoxy-4-[3-(3-methyl-4-oxo-2-thioxo-5-thiazolinylidene)-1-butenyl]phenoxyacetic acid (from the product of Example 55)

Yield 94.0%
Brown crystals, m.p. 241°–245° C. (dec.)
IR(KBr) cm$^{-1}$: 3412, 1748, 1513, 1279, 1253, 1143, 1126
NMR(DMSOd$_6$) δ: 2.21(s, 3H), 3.36(s, 3H), 3.84(s, 3H), 4.73(s, 2H), 6.92(d, 1H), 7.15–7.19(2H), 7.34(d, 1H), 8.50(d, 1H), 13.04(br, s, 1H)

EXAMPLE 79

4-Bromo-2-[3-(4-oxo-2-thioxo-5-thiazolinylidene)-1-butenyl]phenoxyacetic acid (from the product of Example 56)

Yield 99.5%
Orange crystals, m.p. 245° C.
IR(KBr) cm$^{-1}$: 3450, 1685, 1548, 1440, 1200, 680
NMR(DMSO-d$_6$) δ: 2.13(s, 3H), 4.74(s, 2H), 6.90(d, 1H), 7.35–7.84(3H), 8.63(d, 1H)

EXAMPLE 80

2,4-Dichloro-6-[3-(4-oxo-2-thioxo-5-thiazolinylidene)-1-butenyl]phenoxyacetic acid (from the product of Example 57)

Yield 97.4%
Light brown crystals, m.p. 263° C.
IR(KBr) cm$^{-1}$: 3450, 1685, 1568, 1453, 1210, 1050
NMR(DMSOd$_6$) δ: 2.17(s, 3H), 4.58(s, 2H), 7.53(s, 2H), 7.74(d, 1H), 8.54(d, 1H), 13.40(br, s, 1H)

EXAMPLE 81

2,4-Dibromo-6-[3-(4-oxo-2-thioxo-5-thiazolinylidene)-1-butenyl]phenoxyacetic acid (from the product of Example 58)

Yield 96.4%
Reddish brown crystals, m.p. 260°–270° C.
IR(KBr) cm$^{-1}$: 3450, 1685, 1557, 1445, 1200
NMR(DMSO-d$_6$) δ: 2.15(s, 3H), 4.55(s, 2H), 7.62–7.80(3H), 8.50(d, 1H), 13.00(br, s, 1H)

EXAMPLE 82

2-Methoxy-5-[3-(4-oxo-2-thioxo-5-thiazolinylidene)-1-butenyl]phenoxyacetic acid (from the product of Example 59)

Yield 34.0%
Reddish brown powders, m.p. 244°–246° C. (ec.)
IR(KBr) cm$^{-1}$: 3412, 1736, 1599, 1545, 1513, 1263, 1231, 1195, 680

EXAMPLE 83

2-Methoxycarbonylmethoxy-4-[3-(4-oxo-2-thioxo-5-thiazolinylidene)-1-butenyl]phenoxyacetic acid Isomer A (from Isomer A of Example 60)

Yield 99.0%
Red crystals, m.p. 299° C. (dec.)
IR(KBr) cm$^{-1}$: 3430, 1695, 1605, 1515, 1420, 1203, 675

Isomer B (from Isomer B of Example 60)

Yield 91.7%
Red crystals, m.p. 314° C. (dec.)
IR(KBr) cm$^{-1}$: 3450, 1693, 1600, 1550, 1515, 1430, 1230, 1200, 678
NMR(DMSOd$_6$) δ: 2.20(s, 3H), 4.72(s, 4H), 6.93(d, 1H), 7.10–7.30(m, 3H), 8.45(d, 1H)

EXAMPLE 84

2-[2-Propyl-3-(4-oxo-2-thioxo-5-thiazolinylidene)-1-propenyl]phenoxyacetic acid (from the product of Example 61)

Yield 24.2%
Orange powders, m.p. 234°–238° C. (dec.)
IR(KBr) cm$^{-1}$: 3430, 1702, 1597, 1563, 1224

EXAMPLE 85

4-Isopropyl-2-[3-(4-oxo-2-thioxo-5-thiazolinylidene)-1-butenyl]phenoxyacetic acid (from the product of Example 62)

Yield 84.0%
Yellowish brown crystals, m.p. 264°–268° C. (dec.)
IR(KBr) cm$^{-1}$: 3422, 1718, 1670, 1442, 1210, 676
NMR(DMSOd$_6$) δ: 1.21(d, 6H), 6H), 2.17(s, 3H), 2.81–2.91(m, 1H), 4.75(s, 2H), 6.88(d, 1H), 7.17(d, 1H), 7.24–7.60(2H), 8.59(d, 1H), 13, 18(br, s, 1H)

EXAMPLE 86

2-[2-Methyl-3-(4-oxo-2-thioxo-5-thiazolinylidene)-1-propenyl]phenoxyacetic acid (from the product of Example 63)

Yield 54.3%
Yellow powders, m.p. 224°–228° C. (dec.)
IR(KBr) cm$^{-1}$: 3398, 3222, 1730, 1713, 1575, 1438, 1220, 1188
NMR(DMSOd$_6$) δ: 2.16(s, 3H), 4.71(s, 2H), 6.90–7.40(6H), 12.88(br, s, 1H), 13.74(br, s, 1H)

EXAMPLE 87

2,6-Dimethyl-4-[3-(4-oxo-2-thioxo-5-thiazolinylidene)-1-butenyl]phenoxyacetic acid (from the product of Example 64)

Yield 70.0%
Yellow crystals, m.p. 269°–273° C. (dec.)
IR(KBr) cm$^{-1}$: 3424, 1722, 1703, 1555, 1440, 1218, 1152

EXAMPLE 88

4-Methoxy-2-[3-(4-oxo-2-thioxo-5-thiazolinylidene)-1-butenyl]phenoxyacetic acid (from the product of Example 65)

Yield 84.9%
Brown crystals, m.p. 261°–263° C. (dec.)
IR(KBr) cm$^{-1}$: 1 3414, 1731, 1713, 1497, 1449, 1214
NMR(DMSOd$_6$) δ: 2.16(s, 3H), 3.76(s, 3H), 4.72(s, 2H), 6.93(s, 2H), 7.10(s, 1H), 7.55(d, 1H), 8.55(d, 1H), 13.05(br, s, 1H), 13.50(br, s, 1H)

EXAMPLE 89

4-Trifluoromethyl-2-[3-(4-oxo-2-thioxo-5-thiazolinylidene)-1-butenyl]phenoxyacetic acid (from the product of Example 66)

Yield 75.4%
Orange crystals, m.p. 267°–269° C. (dec.)
IR(KBr) cm$^{-1}$: 3426, 1705, 1342, 1265, 1201, 1132
NMR(DMSO-d$_6$): 2.17(s, 3H), 4.93(s, 2H), 7.17(d, 1H), 7.49(d, 1H), 7.67(d, 1H), 7.82(s, 1H), 8.65(d, 1H), 13.25(br, s, 1H), 13.55(br, s, 1H)

PHARMACEUTICAL EXAMPLE 1

| Tablets (one tablet) | |
| --- | --- |
| N-{2-(4-oxo-2-thioxo-5-thiazolidinylidene)propionyl}anthranilic acid (active ingredient) | 10 mg |
| Lactose | 67 mg |
| Crystalline cellulose | 15 mg |
| Cornstarch | 7 mg |
| Magnesium stearate | 1 mg |
| | 100 mg |

The above components were uniformly blended to form a powder for direct tabletting. The powder was compressed on a rotary tablet machine to yield tablets each weighing 100 mg and having a diameter of 6 mm.

PHARMACEUTICAL EXAMPLE 2

| Granules (one divided form) | |
| --- | --- |
| N-{2-(4-oxo-2-thioxo-5-thiazolidinylidene)propionyl}anthranilic acid (active ingredient) | 10 mg |
| Lactose | 90 mg |
| Cornstarch | 50 mg |
| Crystalline cellulose | 50 mg |
| Hydroxypropylcellulose | 10 mg |
| Ethanol | 90 mg |

The active ingredient, lactose, cornstarch and cellulose were uniformly blended and a solution of hydroxypropylcellulose in ethanol was added. The resulting mixture was kneaded and granulated according to extrusion granulation method and the granules were dried in a dryer at ° C. The dried granules were sieved out to a grain size of 297 μm–1460 μm to form granules. One divided form contains 200 mg.

PHARMACEUTICAL EXAMPLE 3

| Injectable solutions | |
|---|---|
| N-{2-(4-oxo-2-thioxo-5-thiazolidinyl-idene)propionyl}anthranilic acid (active ingredient) | 1 mg |
| Sodium chloride | 10 mg |
| Distilled water | ad lib. |
| Total | 1.0 ml |

Sodium chloride and the active ingredient were dissolved in distilled water to make up a total to 1.0 ml.

PHARMACEUTICAL EXAMPLE 4

| Suppositories | |
|---|---|
| N-{2-(4-oxo-2-thioxo-5-thiazolidinyl-idene)propionyl}anthranilic acid (active ingredient) | 2 g |
| Polyethylene glycol 4000 | 20 g |
| Glycerol | 78 g |
| Total | 100 g |

Glycerol was added to the active ingredient and then polyethylene glycol 4000 was added. The mixture was molten with heating and injected into a suppository dio and solidified by cooling to prepare suppositories, each weighing 1.5 g.

Inhibitory Activity Against Aldose Reductase

The compounds of the present invention were evaluated for the inhibitory activity against aldose reductase according to the following assay procedure.

Assay Procedure

Enzyme activity was assayed according to the modification [Biochemical Pharmacology, 25, 2505 (1976)] of the method described in J. Biol. Chem., 240, 877–882 (1965).

SD strain male rats were sacrificed by decapitation, the lenses were excised and homogenized in cold distilled water. The homogenate was then centrifuged and the supernatant was used as the crude aldose reductase solution.

Separately, a 0.1 M sodium phosphate buffer (pH 6.2) containing 0.4 M ammonium sulfate was prepared at 30° C. In this buffer were dissolved the present compound, the crude aldose reductase solution and nicotinamide-adenine dinucleotide phosphate, reduced form (NADPH). The mixture was preincubated at 30° C. for 3 minutes and the reaction was initiated by addition of D,L-glyceraldehyde. In this case, the concentration of the present compound dissolved was $10^{-5}$ M and $10^{-6}$ M, respectively. The total amount of the assay mixture was 1.0 ml, containing 0.16 mM of NADPH, 10 mM of D,L-glyceraldehyde and 0.010–0.016 units of aldose reductase.

The inhibitory activity of the present compounds against aldose reductase was measured using each 1.0 ml of the reaction mixture containing the present compound in the above concentration. In this measurement, the rate of NADPH oxidation was followed by recording the decrease in absorbance at 340 nm. The inhibitory activity of the present compounds against aldose reductase as measured was expressed in percentage of inhibition (%) as a relative activity based on a control value. The results are shown in the following table.

| Test compounds | | Percentage of inhibition (%) | |
|---|---|---|---|
| Example No. | Form | $10^{-5}$ M | $10^{-6}$ M |
| 2 | | 72.0 | 48.6 |
| 3 | Isomer A | 77.1 | 29.7 |
| | Isomer B | 80.5 | 34.5 |
| 4 | | 62.6 | 29.9 |
| 6 | Isomer A | 35.0 | — |
| 7 | | 50.9 | — |
| 8 | Isomer A | 57.9 | — |
| | Isomer B | 43.1 | — |
| 12 | | 42.8 | — |
| 13 | Isomer A | 56.0 | — |
| | Isomer B | 54.3 | — |
| 15 | | 66.7 | 35.3 |
| 17 | | 77.6 | 35.9 |
| 18 | | 84.0 | 62.6 |
| 19 | | 34.6 | — |
| 20 | | 84.0 | 43.9 |
| 21 | Isomer A | 94.9 | 78.3 |
| | Isomer B | 89.8 | — |
| 22 | | 88.1 | 41.9 |
| 23 | | 64.6 | — |
| 25 | | 82.0 | 32.9 |
| 26 | Isomer A | 92.0 | 68.9 |
| | Isomer B | 52.1 | — |
| 27 | Isomer A | 90.6 | 53.1 |
| | Isomer B | 83.8 | 45.9 |
| 28 | | 33.0 | — |
| 29 | | 82.8 | 38.5 |
| 30 | | 73.0 | — |
| 31 | | 83.6 | 39.8 |
| 32 | | 92.5 | 84.7 |
| 33 | Isomer A | 42.9 | — |
| | Isomer B | 30.5 | — |
| 34 | | 80.8 | 35.5 |
| 35 | | 72.3 | — |
| 36 | | 94.0 | 80.0 |
| 37 | | 56.4 | — |
| 38 | Isomer A | 95.7 | 86.8 |
| | Isomer B | 94.5 | 77.9 |
| | | 62.6 | 50.9 |
| 40 | | 38.8 | — |
| 41 | | 86.2 | 48.5 |
| 42 | | 54.2 | 33.8 |
| 43 | | 48.9 | 26.1 |
| 44 | | 39.1 | — |
| 45 | | 48.9 | — |
| 46 | | 34.3 | — |
| 48 | | 69.1 | — |
| 49 | | 80.0 | 30.5 |
| 50 | | 48.0 | — |
| 51 | Isomer A | 51.4 | — |
| | Isomer B | 58.7 | — |
| 53 | | 71.3 | 32.0 |
| 55 | Isomer A | 38.1 | 23.8 |
| | Isomer B | 47.5 | 24.3 |
| 56 | | 63.9 | 27.1 |
| 60 | Isomer A | 61.5 | 27.7 |
| | Isomer B | 70.3 | 30.4 |
| 61 | Isomer A | 61.8 | 28.7 |
| | Isomer B | 77.2 | 39.0 |
| 62 | Isomer A | 48.3 | — |
| | Isomer B | 66.7 | — |
| 63 | | 80.5 | 32.2 |
| 65 | | 55.2 | 34.3 |
| 66 | | 79.9 | 45.6 |
| 67 | | 95.3 | 79.4 |
| 68 | | 93.7 | 82.4 |
| 69 | | 78.4 | 46.4 |
| 70 | | 87.4 | 62.2 |
| 71 | | 73.8 | — |
| 72 | | 80.1 | 24.8 |
| 73 | | 59.2 | — |
| 74 | | 74.3 | — |
| 75 | | 95.3 | 87.6 |
| 76 | | 88.5 | 58.6 |
| 77 | | 82.8 | 41.4 |
| 78 | | 87.1 | 65.9 |

-continued

| Test compounds | | Percentage of inhibition (%) | |
|---|---|---|---|
| Example No | Form | $10^{-5}$ M | $10^{-6}$ M |
| 79 | | 95.8 | 86.1 |
| 80 | | 86.6 | 43.0 |
| 81 | | 75.4 | — |
| 82 | | 67.6 | 22.1 |
| 83 | Isomer A | 82.4 | 43.4 |
|  | Isomer B | 75.8 | 36.8 |
| 84 | | 92.0 | 77.6 |
| 85 | | 92.0 | 77.6 |
| 86 | | 89.7 | 69.6 |
| 87 | | 89.6 | 60.5 |
| 88 | | 93.3 | 79.1 |
| 89 | | 92.9 | 85.7 |

What is claimed is:

1. A rhodanine derivative of formula (I)

$$\text{HN} \overset{\text{O}}{\underset{\text{S}}{\diagdown}} \overset{}{\underset{\text{S}}{\diagup}} = \overset{R^1}{\underset{R^2}{}} \quad (I)$$

wherein
R$^1$ is hydrogen, C$_1$-C$_8$ alkyl, carboxyl (C$_1$-C$_4$) alkyl or (C$_1$-C$_4$) alkoxycarbonyl (C$_1$-C$_4$) alkyl;
R$^2$ is CH$_{2n}$ CONHR$^{4'}$ (n is 0 or 1-4); and
R$^{4'}$ is a phenyl group substituted by carboxyl or (C$_1$-C$_3$) alkoxycarbonyl, or a pharmaceutically acceptable salt thereof.

2. A compound of claim 1 wherein R$^2$ is —CONHR$^{4'}$.

3. A compound of claim 1 wherein R$^2$ is CH$_{2n}$ CONHR$^{4'}$, n is 1 to 3.

4. A pharmaceutical composition having an inhibitory activity against aldose reductase, which comprises as an active ingredient a rhodanine derivative of formula (I)

$$\text{HN} \overset{\text{O}}{\underset{\text{S}}{\diagdown}} \overset{}{\underset{\text{S}}{\diagup}} = \overset{R^1}{\underset{R^2}{}} \quad (I)$$

wherein R$^1$ is hydrogen, C$_1$-C$_8$ alkyl, carboxy (C$_1$-C$_4$) alkyl or (C$_1$-C$_4$) alkoxycarbonyl (C$_1$-C$_4$) alkyl;
R$^2$ is CH$_{2n}$ CONHR$^{4'}$ (n is 0 or 1-4); and
R$^{4'}$ is a phenyl group substituted by carboxyl or (C$_1$-C$_3$) alkoxycarbonyl, or a pharmaceutically acceptable salt thereof, associated with one or more pharmaceutically acceptable additives therefor.

5. A compound of claim 4 wherein R$_2$ is —CONHR$^{4'}$.

6. A compound of claim 4 wherein R$^2$ is CH$_{2n}$ CONHR$^{4'}$, n is 1 to 3.

* * * * *